US010736765B1

(12) United States Patent
Lahiff et al.

(10) Patent No.: US 10,736,765 B1
(45) Date of Patent: Aug. 11, 2020

(54) KNEE ORTHOSIS WITH VARIABLE STIFFNESS AND DAMPING

(71) Applicants: Christina-Anne Kathleen Lahiff, St. Petersburg, FL (US); Kyle Brandon Reed, Tampa, FL (US); Seok Hun Kim, Tampa, FL (US); Tyagi Ramakrishnan, Tampa, FL (US)

(72) Inventors: Christina-Anne Kathleen Lahiff, St. Petersburg, FL (US); Kyle Brandon Reed, Tampa, FL (US); Seok Hun Kim, Tampa, FL (US); Tyagi Ramakrishnan, Tampa, FL (US)

(73) Assignee: University of South Florida, Tampa, FL (US)

( * ) Notice: Subject to any disclaimer, the term of this patent is extended or adjusted under 35 U.S.C. 154(b) by 588 days.

(21) Appl. No.: 15/357,327

(22) Filed: Nov. 21, 2016

Related U.S. Application Data

(60) Provisional application No. 62/258,166, filed on Nov. 20, 2015.

(51) Int. Cl.
*A61F 5/01* (2006.01)

(52) U.S. Cl.
CPC .... *A61F 5/0125* (2013.01); *A61F 2005/0169* (2013.01); *A61F 2005/0179* (2013.01)

(58) Field of Classification Search
CPC ............ A61F 5/0125; A61F 2005/0169; A61F 2005/0179; A61F 5/01; A61F 5/0102; A61F 5/0123; A61F 5/0104; A61F 5/0106; A61F 2005/0137; A61F 2005/0197; A61H 3/00; A61H 2003/001; A61H 2003/002

USPC .......................................................... 602/27
See application file for complete search history.

(56) References Cited

U.S. PATENT DOCUMENTS

| | | | |
|---|---|---|---|
| 3,528,412 A * | 9/1970 | McDavid ............. | A61F 5/0125 2/22 |
| 5,277,281 A | 1/1994 | Carlson et al. | |
| 6,517,503 B1 | 2/2003 | Naft et al. | |
| 8,287,477 B1 | 10/2012 | Herr et al. | |
| 2008/0108918 A1* | 5/2008 | Joutras ..................... | A61H 1/02 601/34 |
| 2008/0200856 A1* | 8/2008 | Cadichon .............. | A61F 5/0123 602/32 |

(Continued)

FOREIGN PATENT DOCUMENTS

WO    WO-2008080232 A1 *    7/2008    ............... A61F 2/64

OTHER PUBLICATIONS

Kobayashi et al., Design of a stiffness-adjustable ankle-foot orthosis and its effect on ankle joint kinematics in patients with stroke, Gait & Posture, 33, 2011, pp. 721-723.

(Continued)

*Primary Examiner* — Alireza Nia
*Assistant Examiner* — Sophia T Chang
(74) *Attorney, Agent, or Firm* — Smith & Hopen, P.A.; Steven M. Forte; Nilay J. Choksi

(57) ABSTRACT

A small, lightweight, adjustable knee orthosis for restoring gait symmetry. The orthosis includes a rotary damper for variable damping at the knee joint of the user, and a spring member for variable stiffness at the knee joint of the user. An exemplary application of the device is as a rehabilitation device for individuals who have had a stroke, as the device is designed to induce larger knee flexion as an aftereffect.

11 Claims, 10 Drawing Sheets

(56) References Cited

U.S. PATENT DOCUMENTS

2013/0226048 A1    8/2013   Unluhisarcikli et al.
2015/0005686 A1    1/2015   Kazerounian et al.

OTHER PUBLICATIONS

Nikitczuk, Jason, et al. "Active knee rehabilitation orthotic device with variable damping characteristics implemented via an electrorheological fluid." Mechatronics, IEEE/ASME Transactions on 15.6 (2010): 952-960.

Nikiczuk et al., Design, Control and Human Testing of an Active Knee Rehabilitation Orthotic Device, 2007 IEEE International Conference on Robotics and Automation Roma, Italy, Apr. 10-14, 2007, pp. 4126-4133.

Hassani et al., Powered orthosis for lower limb movements assistance and rehabilitation, Control Engineering Practice 26 (2014) 245-253.

Abolhasani, H., Ansari, N. N., Naghdi, S., Mansouri, K, Ghotbi, N., & Hasson, S. (2012)Comparing the validity of the Modified Modified Ashworth Scale (MMAS) and the Modified Tardieu Scale (MTS) in the assessment of wrist flexor spasticity in patients with stroke: protocol for a neurophysiological study. BMJ open, 2(6).

Balasubramanian, C. K; Bowden, M. G.; Neptune, R. R. & Kautz, S. A. (2007), "Relationship between step length asymmetry and walking performance in subjects with chronic hemiparesis," Archives of physical medicine and rehabilitation 88(1),43-49.

Belda-Lois, J.-M.; Mena-del Horno, S.; Bermejo-Bosch, L; Moreno, J. C.; Pons, J. L.; Farina, D.; Iosa, M.; Molinari, M.; Tamburella, F.; Ramos, A. & others (2011), "Rehabilitation of gait after stroke: a review towards a top-down approach," Journal of neuroengineering and rehabilitation 8(1), 66.

Blackburn, Marjan, Paulette van Vliet, and Simon P. Mockett. "Reliability of measurements obtained with the modified Ashworth scale in the lower extremities of people with stroke." Physical therapy 82.1 (2002): 25-34.

Bohannon, R. W. & Smith, M. B. (1987), "Interrater reliability of a modified Ashworth scale of muscle spasticity," Physical therapy 67(2), 206-207.

Bowden, M. G.; Balasubramanian, C. K.; Neptune, R. R. & Kautz, S. A. (2006), "Anterior-posterior ground reaction forces as a measure of paretic leg contribution in hemiparetic walking," Stroke 37(3), 872-876.

Brandstater, M.; De Bruin, H.; Gowland, C. & Clark, B. (1983), "Hemiplegic gait: analysis of temporal variables.," Archives of physical medicine and rehabilitation 64(12), 583-587.

Dewar, M. & Judge, G. (1980), "Temporal asymmetry as a gait quality indicator," Medical and Biological Engineering and Computing 18(5), 689-693.

Donelan, J. M.; Kram, R. & Kuo, A. D. (2002), "Mechanical work for step-to-step transitions is a major determinant of the metabolic cost of human walking," Journal of Experimental Biology 205(23), 3717-3727.

Gitter, A.; Czerniecki, J. & Weaver, K. (1995), "A Reassessment of Center-of-Mass Dynamics As a Determinate of the Metabolic Inefficiency of Above-Knee Amputee Ambulation," American Journal of Physical Medicine and Rehabilitation 74(5).

Gordon, C.; Fletcher, W.; Jones, G. M. & Block, E. (1995), "Adaptive plasticity in the control of locomotor trajectory," Experimental Brain Research 102(3), 540-545.

Handzic, Ismet, "Design and Testing of a Motion Controlled Gait Enhancing Mobile Shoe (GEMS) for Rehabilitation" (2011). Graduate Theses and Dissertations.

Handzic, I.; Barno, E; Vasudevan, E. V. & Reed, K. B. (2011), "Design and Pilot Study of a Gait Enhancing Mobile Shoe," Journal of Behavioral Robotics, Special Issue on Assistive Robotics 2(4), 193-201.

Handzic, Ismet, and K. B. Reed, "Comparison of the Passive Dynamics of Walking on Ground, Tied-belt and Split-belt Treadmills, and via the Gait Enhancing Mobile Shoe (GEMS)," Proc. of the 13th Intl. Conf. on Rehabilitation Robotics (ICORR), Seattle, USA, Jun. 2013, pp. 1-6.

Herzog, W.; Nigg, B. M.; Read, L. J. & Olsson, E. (1989), "Asymmetries in ground reaction force patterns in normal human gait.," Medicine and Science in Sports and Exercise 21(1), 110-114.

Hoffman, M. D.; Sheldahl, L. M.; Buley, K. J. & Sandford, P. R. (1997), "Physiological comparison of walking among pilateral above-knee amputee and able-bodied subjects, and a model to account for the differences in metabolic cost," Archives of Physical Medicine and Rehabilitation 78(4), 385-392.

Huang, C.; Jackson, J.; Moore, N.; Fine, P.; Kuhlemeier, K.; Traugh, G. & PT, S. (1979), "Amputation: energy cost of ambulation," Arch Phys Med Rehabil 60(1), 18-24.

Kim, C. M. & Eng, J. J. (2003), "Symmetry in vertical ground reaction force is accompanied by symmetry in temporal but not distance variables of gait in persons with stroke," Gait & Posture 18(1), 23-28.

Kim, S. & Reed, K. (2013), Robot-Assisted Balance Training for Gait Modification "2013 IEEE International Conference on Rehabilitation Robotics", pp. 1-4.

Lin, David C., and William Zev Rymer. "A quantitative analysis of pendular motion of the lower leg in spastic human subjects." Biomedical Engineering, IEEE Transactions on 38.9 (1991): 906-918.

Lord, S. E.; McPherson, K.; McNaughton, H. K.; Rochester, L. & Weatherall, M. (2004), "Community ambulation after stroke: how important and obtainable is it and what measures appear predictive?" Archives of physical medicine and rehabilitation 85(2), 234-239.

McIntosh, J. (2015). "What is stroke? What causes strokes?." Medical News Today. Retrieved from http://www.medicalnewstoday.com/articles/7624.php, pp. 1-13.

Olney, Sandra J., and Carol Richards. "Hemiparetic gait following stroke. Part I: Characteristics." Gait & Posture 4.2 (1996): 136-148.

Patterson, S. L.; Rodgers, M. M.; Macko, R. F. & Forrester, L. W. (2008), "Effect of treadmill exercise training on spatial and temporal gait parameters in subjects with chronic stroke: a preliminary report," Journal of rehabilitation research and development 45(2), 221-228.

Perry, J.; Garrett, M.; Gronley, J. K. & Mulroy, S. J. (1995), "Classification of walking handicap in the stroke population," Stroke 26(6), 982-989.

Reisman, D.; Wityk, R. & Bastian, A. (2005), "Split-belt treadmill walking adaptation in post-stroke hemiparesis," J. Neurologic Physical Therapy 29, 196.

Roerdink, M.; Lamoth, C. J.; Kwakkel, G.; van Wieringen, P. C. & Beek, P. J. (2007), "Gait coordination after stroke: benefits of acoustically paced treadmill walking," Physical Therapy 87(8), 1009-1022.

Sulzer, James S., et al. "Adaptation to knee flexion torque during gait" Rehabilitation Robotics, 2009. ICORR 2009. IEEE International Conference on. IEEE, 2009, pp. 713-718.

Titianova, E. B. & Tarkka, I. M. (1995), "Asymmetry in walking performance and postural sway in patients with chronic unilateral cerebral infarction," Journal of rehabilitation research and development 32,3236-244.

Vashista, V.; Reisman, D. & Agrawal, S. (2013), "Asymmetric Adaptation in Human Walking using the Tethered Pelvic Assist Device (TPAD)" IEEE International Conference on Rehabilitation Robotics, pp. 1-6.

Vasudevan, E. V. & Kirk, E. M. (2014), Improving Interlimb Coordination Following Stroke: How Can We Change How People Walk (and Why Should We)? "Replace, Repair, Restore, Relieve—Bridging Clinical and Engineering Solutions in Neurorehabilitation," Springer, pp. 195-202.

\* cited by examiner

KNEE ORTHOSIS WITH VARIABLE STIFFNESS AND DAMPING

CROSS-REFERENCE TO RELATED APPLICATIONS

This U.S. Nonprovisional Patent Application claims priority to U.S. Provisional Patent Application No. 62/258,166, entitled "Knee Orthosis with Variable Stiffness and Damping", filed Nov. 20, 2015 by the same inventors, the entirety of which is incorporated herein by reference.

FEDERALLY SPONSORED RESEARCH OR DEVELOPMENT

This invention was made with Government support under Grant No. 1319802 awarded by the National Science Foundation. The government has certain rights in the invention.

BACKGROUND OF THE INVENTION

Field of the Invention

This invention relates, generally, to knee orthosis. More specifically, it relates to rehabilitation devices for restoring gait symmetry.

Brief Description of the Prior Art

Since stroke is a nondiscriminatory occurrence, it can affect anyone at any time (McIntosh, J. (2015). "What is stroke? What causes strokes?" Medical News Today). Individuals having suffered a unilateral stroke can have neuromuscular weakness or paralysis on one side of the body caused by some muscles disengaging and other muscles overexciting. Hyperextension of the knee joint and complete lack of plantar flexion of the ankle joint are common effects after stroke as well. The degree of knee spasticity remaining post stroke is commonly evaluated by physical therapists using the Modified Ashworth Scale. The Modified Ashworth Scale is used to qualify the damping and stiffness levels of those affected by stroke, but it has not been quantified in terms of numerical values.

Stroke survivors can have a difficult time adapting to their new life, especially if they have the side effect of hemiparesis, which is partial neuromuscular paralysis. Hemiparesis often results in asymmetric gait that requires the utilization of various forms of rehabilitation techniques and devices (Handzic, Ismet, and K. B. Reed, "Comparison of the Passive Dynamics of Walking on Ground, Tied-belt and Split-belt Treadmills, and via the Gait Enhancing Mobile Shoe (GEMS)," Proc. of the 13th Intl. Conf. on Rehabilitation Robotics (ICORR), Seattle, USA, June, 2013). The majority of the walking process is governed by the passive dynamics of the legs and body (Donelan, J. M., Kram, R., & Kuo, A. D. (2002), "Mechanical work for step-to-step transitions is a major determinant of the metabolic cost of human walking," Journal of Experimental Biology 205(23), 3717-3727), which generally leads to symmetric walking when both sides of the body are identical.

In an asymmetrically impaired individual, asymmetric control effort is necessary to force symmetric motions. These compensatory motions, such as using alternate arm movements along with torso and hip flexion, are commonly used by disabled individuals. These adaptations often lead to back pain and premature deterioration of joints in individuals with stroke and also cause stresses at the residual limb socket in amputees. An individual with an asymmetric impairment may not be able to sustainably achieve a temporally-, spatially-, and kinetically-symmetric gait.

Spatial and temporal asymmetries in gait occur when the step length of one foot is not equivalent to that of the other (Olney, S. J., and C. Richards. "Hemiparetic gait following stroke. Part I: Characteristics." Gait & Posture 4.2 (1996): 136-148). While more exaggerated asymmetries occur in stroke patients and those who possess central nervous system damage, some asymmetries are inherent in able-bodied persons. A metric-based analysis of asymmetries can be found in a recent manuscript by the current inventors (Tyagi Ramakrishnan & Kyle B Reed, Analysis of Multiple Asymmetries Using Consolidated Metrics, Preprint submitted to Human Movement Science, August 2016).

Rehabilitation facilities, such as the U.S. Department of Veterans Affairs and private hospitals, utilize rehabilitation devices, for example split belt treadmill systems, exoskeletal systems, and active ankle-foot orthosis (Blackburn, Marjan, Paulette van Vliet, and Simon P. Mockett. "Reliability of measurements obtained with the Modified Ashworth scale in the lower extremities of people with stroke." Physical therapy 82.1 (2002): 25-34). However, these rehabilitation avenues have relatively large monetary and physical costs associated with them, along with taking a significant amount of time.

The coordinated limb control during walking is frequently impaired following central nervous system damage, such as suffering a stroke or traumatic brain injury, or physical changes, such as utilization of a cane or wearing a prosthesis. Able-bodied adults generally take equal-sized steps with each leg, offset by about 180°. This offset is commonly referred to as "out-of-phase" coordination. Individuals who have had a stroke or lower-limb amputation often diverge from perfectly out-of-phase walking and have asymmetries in temporal measure (e.g., time spent in double-limb support) and spatial measures (e.g., step length) of interlimb coordination (Balasubramanian, C. K., Bowden, M. G., Neptune, R. R. & Kautz, S. A. (2007), "Relationship between step length asymmetry and walking performance in subjects with chronic hemiparesis," Archives of physical medicine and rehabilitation 88(1), 43-49; Brandstater, M., De Bruin, H., Gowland, C. & Clark, B. (1983), "Hemiplegic gait: analysis of temporal variables," Archives of physical medicine and rehabilitation 64(12), 583-587).

As noted, asymmetric gait patterns are common in stroke victims and amputees, but are more noticeably evident in transfemoral amputees, which are amputees that have lost their leg above the knee joint location (Gitter, A., Czerniecki, J. & Weaver, K. (1995), "A Reassessment of Center-of-Mass Dynamics As A Determinate of the Metabolic Inefficiency of Above-Knee Amputee Ambulation," American Journal of Physical Medicine and Rehabilitation 74(5); Hoffman, M. D., Sheldahl, L. M., Buley, K. J. & Sandford, P. R. (1997), "Physiological comparison of walking among bilateral above-knee amputee and able-bodied subjects, and a model to account for the differences in metabolic cost," Archives of Physical Medicine and Rehabilitation 78(4), 385-392). The asymmetry causes wearers to exert a large amount of effort in order to try to compensate for unwanted, uncontrollable motions (Huang, C.; Jackson, J.; Moore, N.; Fine, P.; Kuhlemeier, K.; Traugh, G. & PT, S. (1979), "Amputation: energy cost of ambulation," Arch Phys Med Rehabil 60(1), 18-24). In the case of stroke victims, the propulsive force of the paretic limb is less than that of the non-paretic limb. Thus, the work and the power of the paretic plantar flexors are, in turn, also lessened (Balasubramanian, C. K., Bowden, M. G., Neptune, R. R. & Kautz, S. A. (2007), "Relationship between step length asymmetry and walking performance in subjects with chronic hemiparesis," Archives of physical medicine and rehabilitation 88(1), 43-49; Bowden, M. G., Balasubramanian, C. K., Neptune, R. R. & Kautz, S. A. (2006), "Anterior-posterior ground reaction forces as a measure of paretic leg contribution in hemiparetic walking," Stroke 37(3), 872-876).

Vertical ground reaction forces also are decreased on the paretic limb relative to the nonparetic limb (Kim, C. M. & Eng, J. J. (2003), "Symmetry in vertical ground reaction force is accompanied by symmetry in temporal but not distance variables of gait in persons with stroke," Gait & Posture 18(1), 23-28). This is emulated in the depreciated weight-bearing of the paretic limb. Current popular asymmetric gait rehabilitation methods include circular treadmill locomotion (Gordon, C., Fletcher, W., Jones, G. M., & Block, E. (1995), "Adaptive plasticity in the control of locomotor trajectory," Experimental Brain Research 102(3), 540-545), split-belt treadmills (Reisman, D., Wityk, R. & Bastian, A. (2005), "Split-belt treadmill walking adaptation in post-stroke hemiparesis," J. Neurologic Physical Therapy 29, 196), split-motion training (Handzic, Ismet, and K. B. Reed, "Comparison of the Passive Dynamics of Walking on Ground, Tied-belt and Split-belt Treadmills, and via the Gait Enhancing Mobile Shoe (GEMS)," Proc. of the 13th Intl. Conf. on Rehabilitation Robotics (ICORR), Seattle, USA, June, 2013), rhythmic cuing (Roerdink, M., Lamoth, C. J., Kwakkel, G., van Wieringen, P. C. & Beek, P. J. (2007), "Gait coordination after stroke: benefits of acoustically paced treadmill walking," Physical Therapy 87(8), 1009-1022), balance training (Vashista, V., Reisman, D. & Agrawal, S. (2013) "Asymmetric Adaptation in Human Walking using the Tethered Pelvic Assist Device (TPAD)" IEEE International Conference on Rehabilitation Robotics"; Kim, S. & Reed, K. (2013), Robot-Assisted Balance Training for Gait Modification "2013 IEEE International Conference on Rehabilitation Robotics"), and others (Belda-Lois, J.-M., Mena-del Horno, S., Bermejo-Bosch, I., Moreno, J. C., Pons, J. L., Farina, D., Iosa, M., Molinari, M., Tamburella, F., Ramos, A. & others (2011), "Rehabilitation of gait after stroke: a review towards a top-down approach," Journal of neuroengineering and rehabilitation 8(1), 66). Traditional rehabilitation interventions, such as locomotive training with and without weight support and physical therapist assistance, have aided in speed, control, and endurance. However, these techniques are typically not effective at restoring symmetry (Vasudevan, E. V. & Kirk, E. M. (2014), Improving Interlimb Coordination Following Stroke: How Can We Change How People Walk (and Why Should We)? "Replace, Repair, Restore, Relieve—Bridging Clinical and Engineering Solutions in Neurorehabilitation," Springer, pp. 195-202). Recent work investigating gait rehabilitation has had a principle focus on two main outcome measures: velocity and symmetry. Walking velocity is indicative of overall gait performance and can be utilized to discern various levels of disability (Lord, S. E., McPherson, K., McNaughton, H. K., Rochester, L. & Weatherall, M. (2004), "Community ambulation after stroke: how important and obtainable is it and what measures appear predictive?" Archives of physical medicine and rehabilitation 85(2), 234-239; Perry, J., Garrett, M., Gronley, J. K. & Mulroy, S. J. (1995), "Classification of walking handicap in the stroke population," Stroke 26(6), 982-989). Symmetry, in contrast, measures the quality of the gait pattern (Dewar, M. & Judge, G. (1980), "Temporal asymmetry as a gait quality indicator," Medical and Biological Engineering and Computing 18(5), 689-693; Patterson, S. L.; Rodgers, M. M.; Macko, R. F. & Forrester, L. W. (2008), "Effect of treadmill exercise training on spatial and temporal gait parameters in subjects with chronic stroke: a preliminary report," Journal of rehabilitation research and development 45(2), 221).

Normal gait has been found to be generally symmetric in the kinematics, dynamics, vertical forces, and spatiotemporal parameters between the two legs (Herzog, W., Nigg, B. M., Read, L. J. & Olsson, E. (1989), "Asymmetries in ground reaction force patterns in normal human gait," Medicine and Science in Sports and Exercise 21(1), 110-114; Titianova, E. B. & Tarkka, I. M. (1995), "Asymmetry in walking performance and postural sway in patients with chronic unilateral cerebral infarction," Journal of rehabilitation research and development 32, 3236-244). Despite these studies, there has been no completely effective rehabilitation apparatus or methodology for correcting an asymmetric gait.

Accordingly, what is needed is knee orthosis with variable stiffness and damping that simulates hemiparetic gait and lead to a rehabilitative device. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved knee orthosis for improving knee flexion is now met by a new, useful, and nonobvious invention.

In an embodiment, the current invention is a knee orthosis with variable damping and stiffness for increasing knee flexion at a knee or knee joint of a user thereof. The knee orthosis includes an upper splint and a lower splint, each of which are elongate and are rigid or semi-rigid. The upper splint is positioned substantially parallel to the user's outer thigh, and the lower splint is positioned substantially parallel to the user's outer calf. A central hub is disposed between the splints and is positioned on a lateral side of the user's knee, where the splints are disposed in hinged relation to each other via the central hub.

The orthosis further includes a rotary damper and a spring member, each positioned on the lateral side of the user's knee at a coupling point where the upper and lower splints rotate relative to each other. For example, the rotary damper can be disposed in outer relation to the central hub, and the spring member may be disposed in outer relation to the rotary damper. The spring member includes an upper spring leg coupled to the upper splint (e.g., via an upper spring post, which may be a bolt, extending outwardly from the upper splint) and a lower spring leg coupled to the lower splint (e.g., via a lower spring post, which may be a bolt, extending outwardly from the lower splint). When the splints rotate relative to each other, the rotary damper provides a damping effect and the spring member (e.g., torsion spring) provides a stiffness. A magnetorheological fluid may be disposed within the rotary damper for enhanced damping effect.

The orthosis may further include a connector component having a first end disposed through a center of the spring member and a second end mounted onto the upper splint. The connector component is removable in order to permit access to the rotary damper and spring member for replacement.

The orthosis may further include one or more upper straps for securing the upper splint to the user's outer thigh and one or more lower straps for securing the lower straps for securing the lower splint to the user's outer calf. In a further embodiment, the upper straps can be a thigh strap for securing a superior end of the upper splint to the user's thigh and an upper patellar strap for securing an inferior end of the upper splint to the user's upper patellar region. In this case, the lower straps can be a lower patellar strap for securing a superior end of the lower splint to the user's lower patellar region and a calf strap for securing an inferior end of the lower splint to the user's calf.

Optionally, the opposite side of the orthosis (i.e., the upper splint, lower splint, central hub, rotary damper, and spring member) may include an upper guide, a lower guide, and a central component disposed between the upper and lower guides. The upper guide is positioned substantially parallel to the user's inner thigh, and the lower guide is positioned substantially parallel to the user's inner calf. The central component is positioned on a medial side of the user's knee, where the upper and lower guides are disposed in hinged relation to each other via the central component. In this case, the upper and lower guides are coupled to the upper and lower splints, such that the upper guide and upper splint move in unison and the lower guide and lower splint move in unison.

In a separate embodiment, the current invention is a knee orthosis with variable damping and stiffness for increasing knee flexion at a knee or knee joint of a user thereof, where the knee orthosis includes any one or more of the foregoing features and characteristics.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
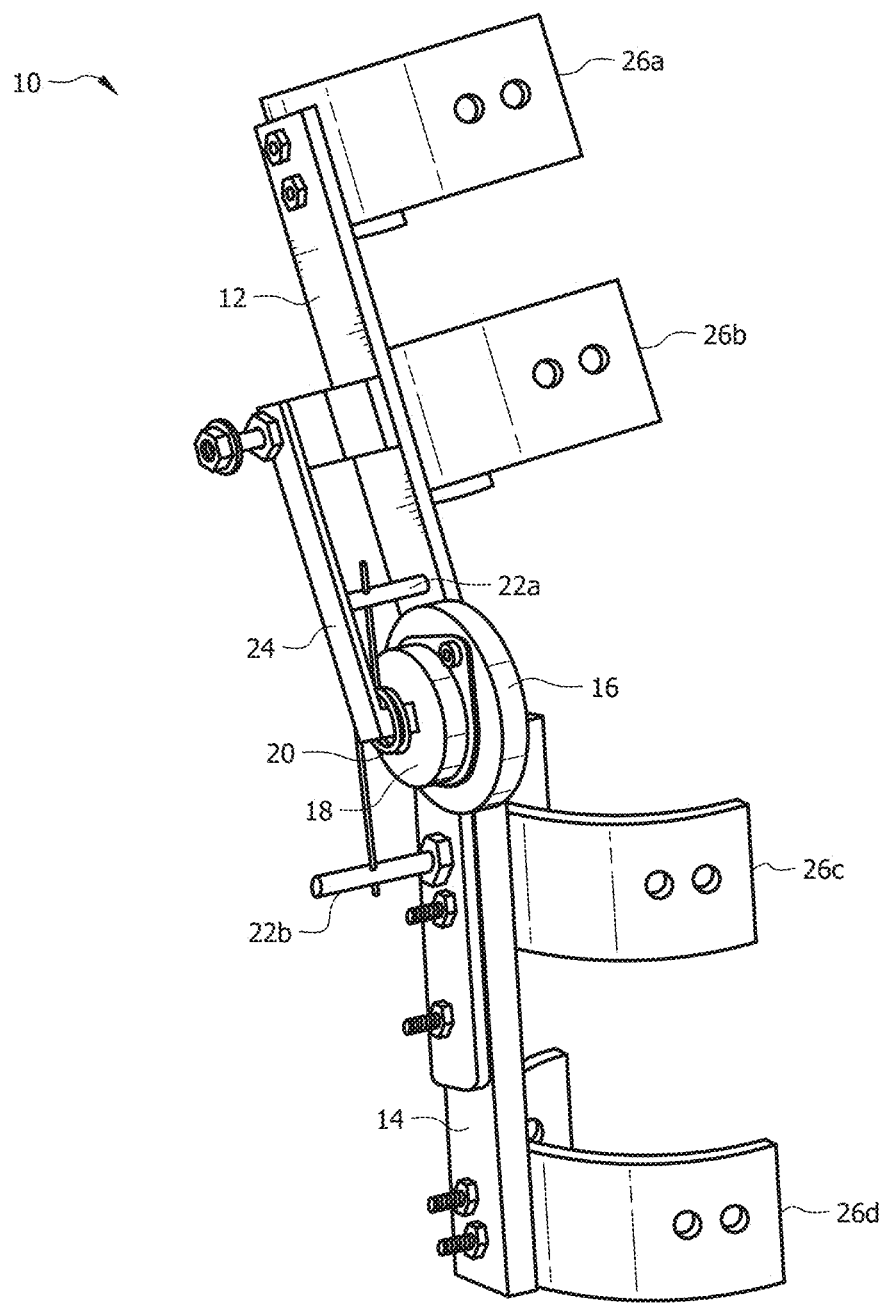
FIG. 1A is an isometric view of a knee orthosis, according to an embodiment of the invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It is an object of the current invention to provide a knee orthosis with variable damping and stiffness at the knee joint. Damping and stiffness of a person affected with stroke has been rated by the Ashworth Scale (Abolhasani, H., Ansari, N. N., Naghdi, S., Mansouri, K., Ghotbi, N., & Hasson, S. (2012). Comparing the validity of the Modified Ashworth Scale (MMAS) and the Modified Tardieu Scale (MTS) in the assessment of wrist flexor spasticity in patients with stroke: protocol for a neurophysiological study. BMJ open, 2(6), e001394), but it has never been quantified. The eventual quantification of the Ashworth Scale would allow for a more personalized design of orthotics that could reduce rehabilitation time.

TABLE 1

Modified Ashworth Scale.

| | |
|---|---|
| Grade 0 | No increase in muscle tone |
| Grade 1 | Slight increase in muscle tone, manifested by a catch and release, or by minimal resistance toward the end of the movement when the affected part(s) is (are) moved in flexion or extension |
| Grade 1+ | Slight increase in muscle tone, manifested by a catch and release, followed by a minimal resistance throughout the remainder (less than half) of the ROM |
| Grade 2 | More marked increase in muscle tone through most of the ROM, but affected part(s) easily moved |
| Grade 3 | Considerable increase in muscle tone, passive movement difficult |
| Grade 4 | Affected part(s) in flexion or extension |

In certain embodiments, the current invention focuses on the development of a custom knee brace that can have variable stiffness and damping at the joint. Studies using this knee brace enabled measurement of the damping and stiffness of various levels of stroke spasticity. The results can also provide a range of values that can be used to quantify the Ashworth Scale.

In certain embodiments, as depicted FIGS. 1A-1E, the current invention is a knee orthosis, generally denoted by the reference numeral 10. Knee orthosis 10 includes upper component 12, lower component 14, and central hub 16. Upper component 12 is an elongate, rigid or semi-rigid splint that is disposed substantially parallel to a length of the thigh of the user when orthosis 10 is in use (see FIG. 1E where upper component 12 is "substantially parallel" to the user's thigh). Lower component 14 is an elongate, rigid or semi-rigid splint that is disposed substantially parallel to a length of the calf of the user when orthosis 10 is in use (see FIG. 1E where lower component 14 is "substantially parallel" to the user's calf). Central hub 16 is disposed between upper component 12 and lower component 14, and provides a hinged component between upper component 12 and lower component 14, such that upper component 12 and lower component 14 are hingedly coupled to one another.

Orthosis 10 further includes rotary damper 18 (e.g., ACE FDN rotary damper), which can be any conventional rotary damper that is capable of controlling deceleration of rotary movement at the pivot point. Rotary damper 18 may control deceleration (via a braking torque) from pivoting of the thigh, pivoting of the calf, or bi-directionally (pivoting of both the thigh and the calf). Disposed on rotary damper 18 is spring member 20, having one end secured to upper post 22a positioned on upper component 12 and lower post 22b positioned on lower component 14. Spring member 20 can be a torsion spring that is biased toward a position of repose, where the user is standing and not walking; alternatively, spring member 20 can be a power spring that is biased toward a position of being coiled.

Optionally, orthosis 10 can include adjustable connector component 24, typically disposed between upper component 12 and central hub 16, including mounting 25 at its superior end to facilitate securement to upper component 12. Connector component 24 provides an additional coupling between upper component 12 and central hub 16, and also provides for a sturdier orthosis frame that facilitates a smoother and more controlled gait for the user. Further, connector component 24 permits rotary damper 18 to be replaced with a different-sized rotary damper, if desired. In order to accommodate for variable stiffness, the inferior end of connector component 24 is positioned in the center of the circular portion of spring member 20 with a deflection angle of 90°, and both upper component 12 and lower component 14 include posts 22a, 22b (e.g., bolts) to lock the spring legs into place. Thus, spring member 20 can be easily replaced with other springs of various stiffnesses at a later time, if needed.

Orthosis 10 further includes a plurality of holsters or straps 26a-26d to secure orthosis 10 to the user's leg. Thigh strap 26a extends laterally from one or both sides of upper component 12 in proximity to a superior edge of orthosis 10 (superior end of upper component 12). Thigh strap 26a is adapted to be secured around a thigh portion of the user. Upper patellar strap 26b extends laterally from one or both sides of upper component 12 in proximity to an inferior end of upper component 12 (near central hub 16). Upper patellar strap 26b is adapted to be secured around a lower thigh/upper patellar portion of the user.

Lower patellar strap 26c extends laterally from one or both sides of lower component 14 in proximity to a superior end of lower component 14 (near central hub 16). Lower patellar strap 26c is adapted to be secured around an upper calf/lower patellar portion of the user. Calf strap 26d extends laterally from one or both sides of lower component 14 in proximity to an inferior edge of orthosis 10 (inferior end of lower component 14). Calf strap 26d is adapted to be secured around a calf portion of the user.

Figure 1B:
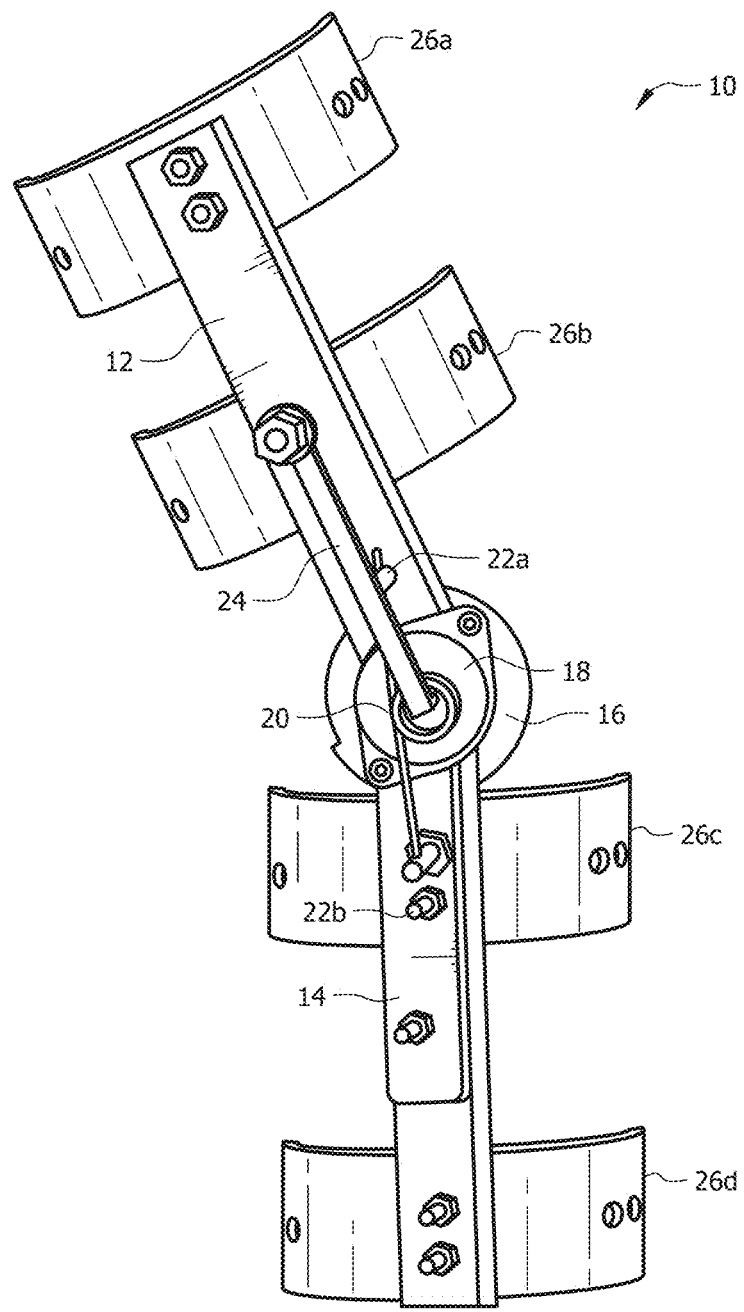
FIG. 1B is an elevated view of a knee orthosis, according to an embodiment of the invention.

For each of thigh strap 26a, upper patellar strap 26b, lower patellar strap 26c, and calf strap 26d, it can extend laterally respectively from both sides of upper component 12 and lower component 14, as can be seen in FIGS. 1A-1B. Straps 26a-26d can then attach to each other respectively around the user's leg, thus securing orthosis 10 on the user's leg, with upper component 12, lower component 14, and central hub 16 positioned on a lateral side of the user's leg. Alternatively, straps 26a-26d can extend respectively from just one side of upper component 12 and lower component 14, wrap around the user's leg, and couple to the other side of upper component 12 and lower component 14.

Figure 1C:
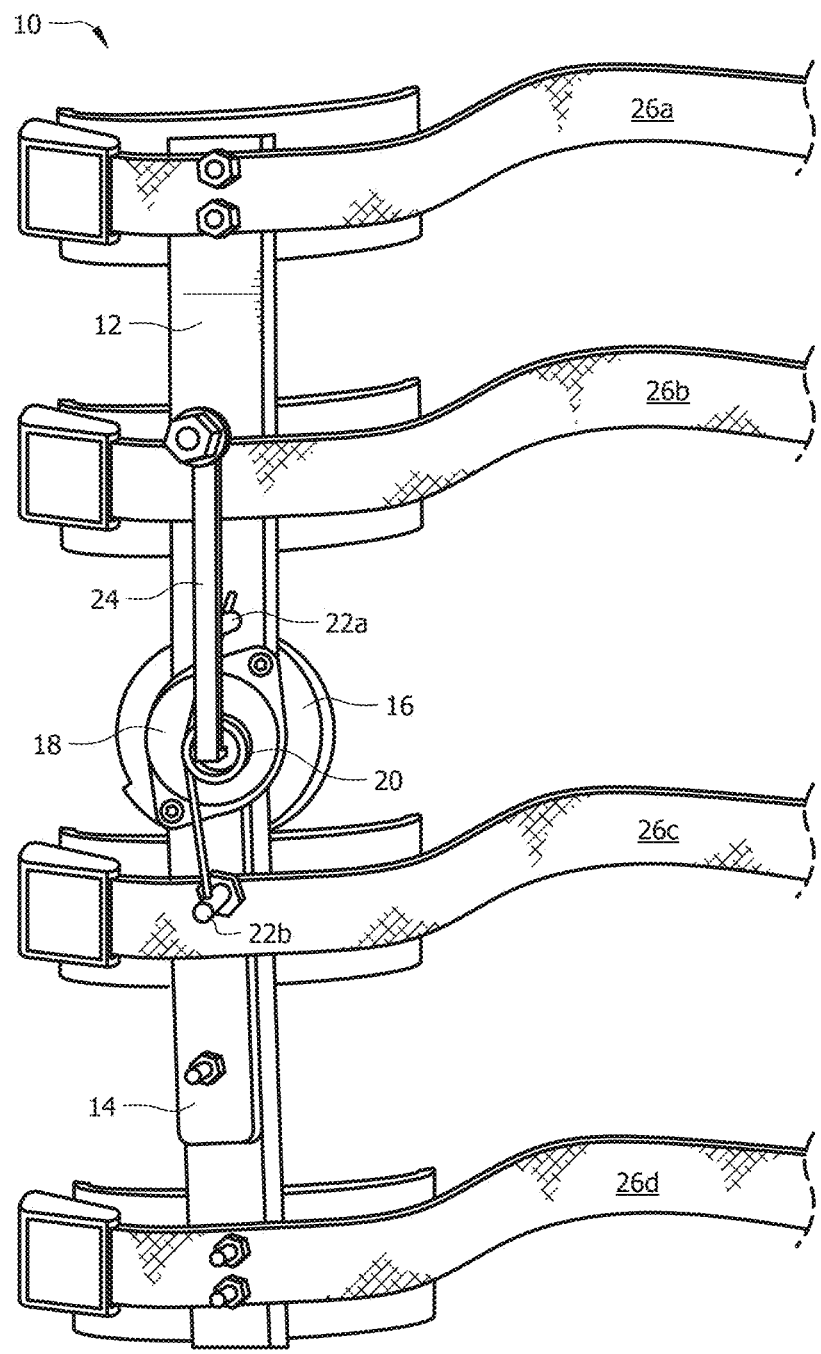
FIG. 1C is an elevated view of a first side of a knee orthosis, according to an embodiment of the invention, where this first side includes a spring-damper mechanism
Figure 1D:
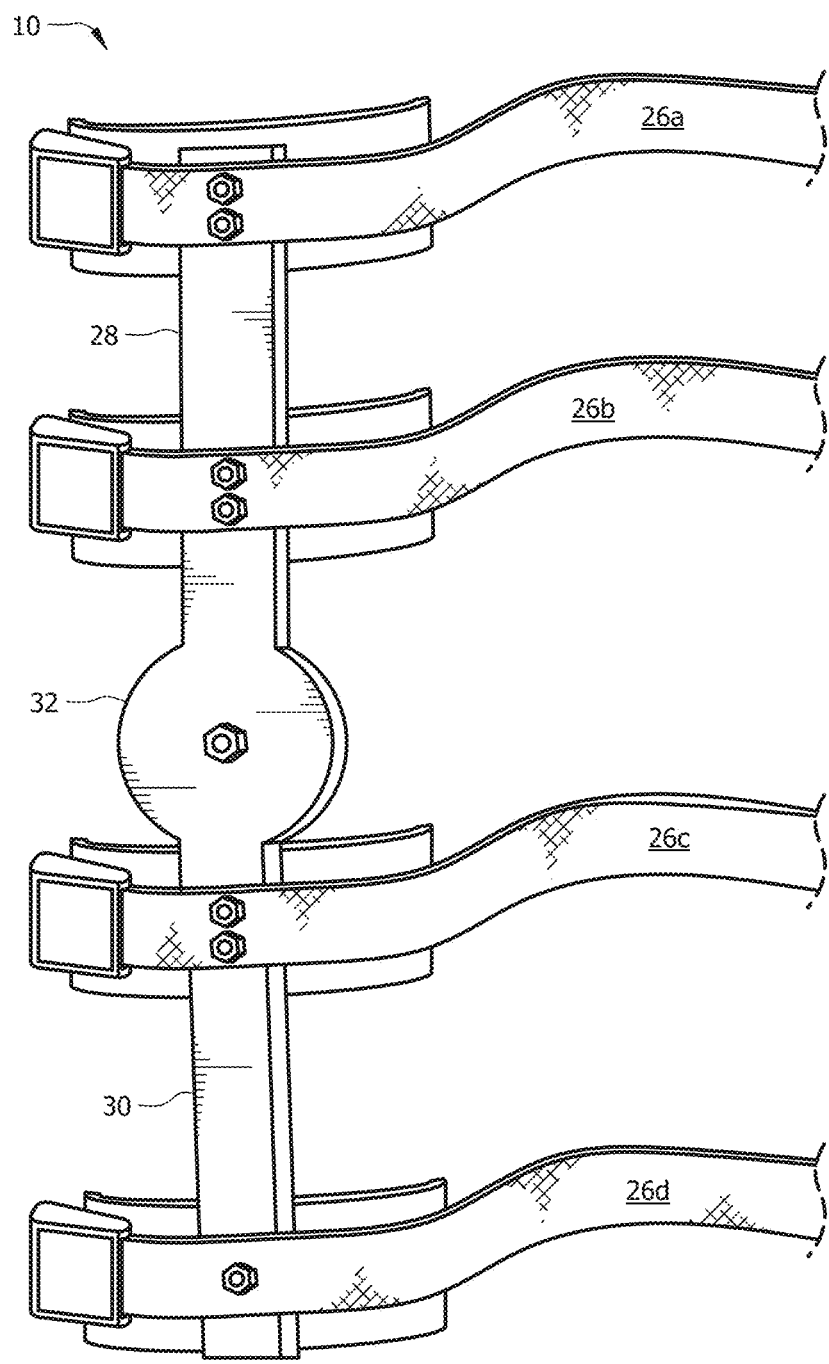
FIG. 1D is an elevated view of a second side of a knee orthosis, according to an embodiment of the invention, where this second side does not include the spring-damper mechanism

Orthosis 10 can be used singularly as seen in FIGS. 1A-1B, where orthosis 10 is positioned on one lateral side of the user's leg; however, orthosis 10 can also be positioned on the other lateral side of user's leg, so that secured on each side of the user's leg is upper component 12, lower component 14, central hub 16, rotary damper 18, and spring member 20. In this case, straps 26a-26d can be coupled together to secure orthosis 10 around the user's leg. FIGS. 1C-1D depict an alternative embodiment or orthosis 10, where FIG. 1C depicts one side of orthosis 10 including the components already described—upper component 12, lower component 14, central hub 16, rotary damper 18, and spring member 20—and FIG. 1D depicts an opposite side of orthosis 10 that functions as a guide for the user's leg. This guide side of orthosis 10 includes rigid or semi-rigid upper component 28, rigid or semi-rigid lower component 30, and central component 32 between upper component 28 and lower component 30. Central component 32 provides a hinged/pivotal relationship between upper component 28 and lower component 30, so that when orthosis 10 is in operation, as the user takes a step, each side of orthosis 10 pivots in synchronization at central hub 16 and center component 32.

The preferred material used to form the orthosis was DELRIN®, a plastic that has material properties similar to that of aluminum, though other suitable materials can be used as well.

Study 1

Clinical evaluation by physical therapy was conducted on the knee orthosis to systematically quantify levels of damping and stiffness corresponding to the Ashworth Scale, a measure of stroke gait determined by physical therapists. The force and range of motion data of the subjects fitted with the orthosis has been collected using the Computer Assisted Rehabilitation Environment (CAREN) system, which will be described later. The four force profiles that were investigated included damping, catch, hysteresis, and stiffness effects. If this orthosis is proven to be effective in this study, it is contemplated herein that the orthosis can ultimately be used in the rehabilitation of individuals with stroke by training them to perform more flexion during gait.

An object of this study and certain embodiments of the current invention to aid individuals with asymmetric impairments in walking with effective gait patterns that balance the gait dynamics with the resulting forces and torques. A mechanism utilized to achieve this goal is the quantification of the Ashworth Scale. To do this, a stroke simulator was used; the stroke simulator was a knee orthosis with variable stiffness and damping, used to evaluate the effects of asymmetric impairments on altering the gait patterns of healthy, able-bodied subjects. It is believed that asymmetries would be induced on able-bodied subjects by the orthosis since only one leg would have a spring-damper mechanism, thus limiting the range of motion. Any inherent asymmetries should also be accounted for in the subject's normal gait, thus adding to the justifications behind gathering data from the system set at the subject's normal walking velocity to obtain a baseline dataset for comparison. Using healthy subjects allows for a reduction of error and uncertainty that would be associated with the variability of disabled individuals. The damping and stiffness allow for the limitation of the flexion at the knee joint to correspond with the limiting ranges of motion of the varying levels of the Ashworth Scale.

The subjects were able-bodied, without any prior knee injury, and were over the age of 18. They ranged in age, gender, and size due the nondiscriminatory nature of a stroke. The variable damping and stiffness were adjusted on the orthosis to simulate the specified level of the Ashworth Scale; in this case, a 1+ was found to be approximately 0.457 kg/mm spring stiffness constant and 8898 g-cm-s/° damping coefficient. A 1+ on the Ashworth Scale corresponds to slight muscle tone increase via catch, and relatively minimal resistance throughout the remainder of the range of motion, which are common side effects of a relatively minor stroke (Blackburn, Marjan, Paulette van Vliet, and Simon P. Mockett. "Reliability of measurements obtained with the Modified Ashworth scale in the lower extremities of people with stroke." Physical therapy 82.1 (2002): 25-34). The goal was to obtain at least three (3) subjects that were to be evaluated, so that a broader range of data could be obtained.

Figure 2:
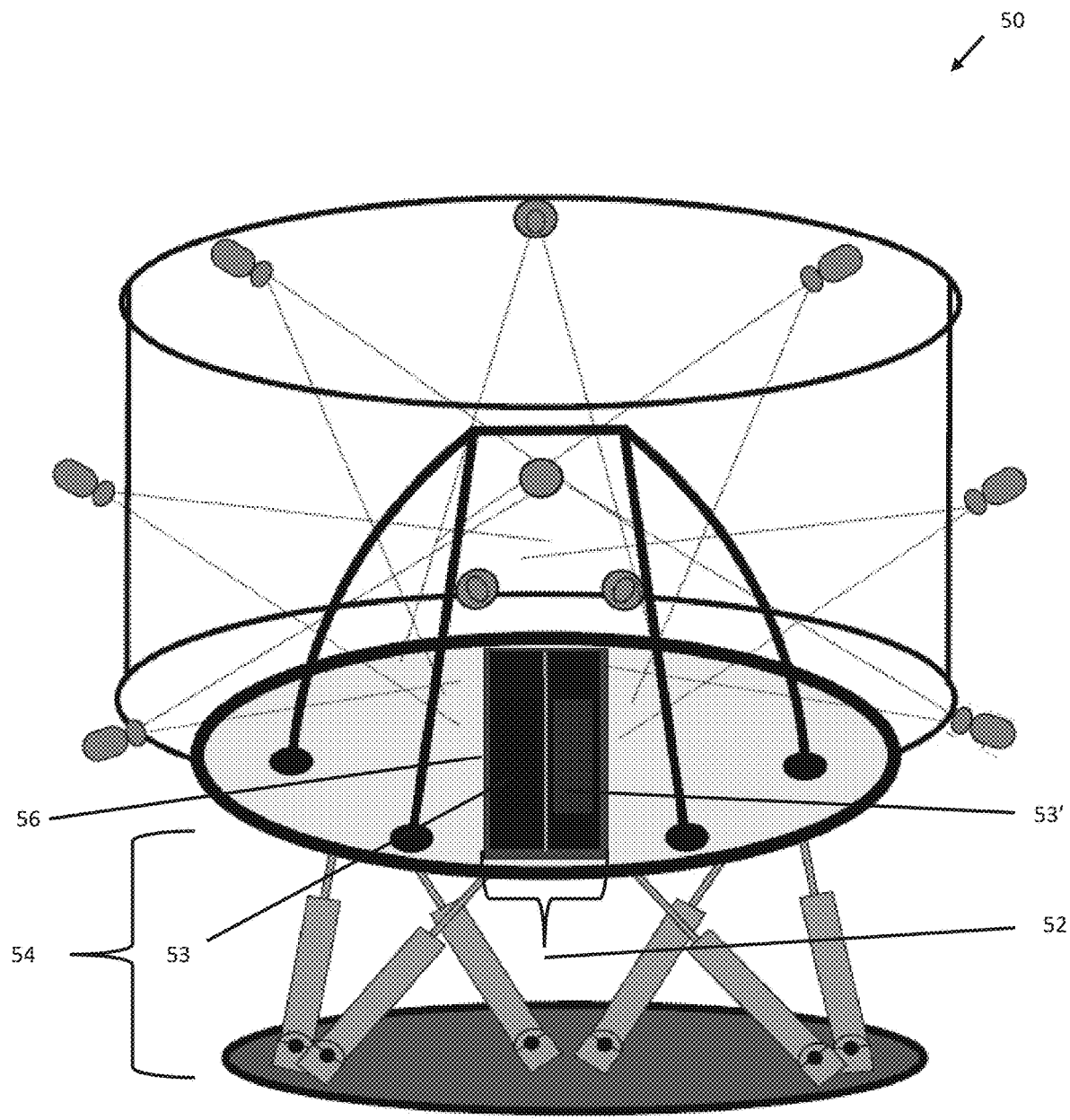
FIG. 2 is a schematic of the CAREN system.

As noted, to study certain embodiments of the current invention, the CAREN system 50 was utilized, a schematic of which can be seen in FIG. 2. Structurally, the CAREN system 50 is a rehabilitative environment that has a split-belt treadmill system 52 mounted on a six-degree of freedom motion base 54 with motion capture and force plates 56. The split-belt treadmill system 52 has two separate moving belts 53, 53' that are able to move at two differing velocities. Split-belt treadmills 52 have often been utilized for rehabilitation of stroke patients that have hemiplegia due to their ability to push one foot at a faster rate than the other, thus aiding in the correction of asymmetric gait patterns (Handzic, Ismet, and K. B. Reed, "Comparison of the Passive Dynamics of Walking on Ground, Tied-belt and Split-belt Treadmills, and via the Gait Enhancing Mobile Shoe (GEMS)," Proc. of the 13th Intl. Conf. on Rehabilitation Robotics (ICORR), Seattle, USA, June, 2013).

Spatial and temporal asymmetries in gait occur when the step length of one foot is not equivalent to that of the other (Olney, Sandra J., and Carol Richards. "Hemiparetic gait following stroke. Part I: Characteristics." Gait & Posture 4.2 (1996): 136-148). While more exaggerated asymmetries occur in stroke patients and those who possess central nervous system damage, some asymmetries are inherent in able-bodied persons. This was part of the reasoning behind gathering data from the CAREN system 50 of the subject's normal gait pattern prior to being fitted with the orthosis. Also, the split-belt treadmill system 52 was not used at different velocities; rather, its capability as a tied-belt system was utilized since the objective of this study was to observe asymmetries induced by the orthosis and not to aid in the correction of asymmetries (Handzic, Ismet, and K. B. Reed, "Comparison of the Passive Dynamics of Walking on Ground, Tied-belt and Split-belt Treadmills, and via the Gait Enhancing Mobile Shoe (GEMS)," Proc. of the 13th Intl. Conf. on Rehabilitation Robotics (ICORR), Seattle, USA, June, 2013).

Functionally, the CAREN system 50 was used to collect force and range of motion data of the asymmetric gait of the subjects. This system presented a safe environment in which force distribution and motion data could be obtained. For safety of the patient, the system has an automated on ramp to transfer the patient to the system, handrails on the platform itself, and a harness to ensure that the patient will not harm himself if he were to trip or fall. Data was collected from the system via utilization of its motion capture infrared cameras and two force plates 56, one on each side of the split belt treadmill 52. The trial data was collected for each subject's normal gait/walking and also for each subject's gait with the current orthosis/brace.

Walking Data without Orthosis.

First, a physical therapist determined the orthosis' induced Ashworth Scale level via clinical evaluation. Next, the subject walked (without orthosis) at his normal pace over ground for a specified distance of 10 m, and his time was recorded. This was performed three (3) times. The average of these three (3) values was then taken in order to determine a baseline walking velocity. Initial baseline evaluation then continued by placing the subject on the CAREN system 50. The subject was fitted with a harness, transferred to the platform via the ramp, and connected to the rail. The system was programmed to have the split belt treadmill 52 velocities bounded together and set at the subject's previously measured baseline velocity. The treadmill begins to move, and the subject was allowed a couple of minutes to become acclimated with the system and make any adjustments prior to data collection. Subsequently, data was collected on any pre-existing spatial or temporal asymmetries, knee flexion angles, and ground reaction forces over a period of five (5) minutes.

Walking Data with Orthosis.

After this "baseline walking" data was collected, the orthosis was fitted onto the subject's right leg. Clinical evaluation by physical therapists was then conducted to assess the level of the Ashworth Scale simulated. Evaluation was conducted by placing the subject on the CAREN system 50, harnessing, and transferring him to the platform. The system was programmed to have the split belt treadmill 52 velocities bounded together and set at the subject's previously measured baseline velocity.

The treadmill was activated, and the subject was allowed a few minutes to become acclimated with the system prior to data collection. Data was then collected on any spatial or temporal asymmetries, knee flexion angles, and ground reaction forces induced by the orthosis over a period of ten (10) minutes.

Post-Orthosis Data.

Immediately following the trial with orthosis worn by each subject, the orthosis was removed from the subject while the subject was still on the treadmill. Post-orthosis data was obtained by having the subject walk on the system for a period of five (5) minutes. The expected aftereffect of the orthosis was an increase in knee flexion of the affected knee and increased force profile that would dissipate within the first minute. Thus, it can be determined whether asymmetry was being induced through the use of the knee orthosis.

This process of obtaining data from the orthosis placed on the right leg was repeated for the orthosis being placed on the left leg. Both legs were tested for the purpose of analyzing if limb dominance was a factor to be considered in gait symmetry. The collected data from both legs was then analyzed to determine if the orthosis is a viable device to induce stroke-like gait patterns and asymmetries.

Results of Study.

Figure 3A:
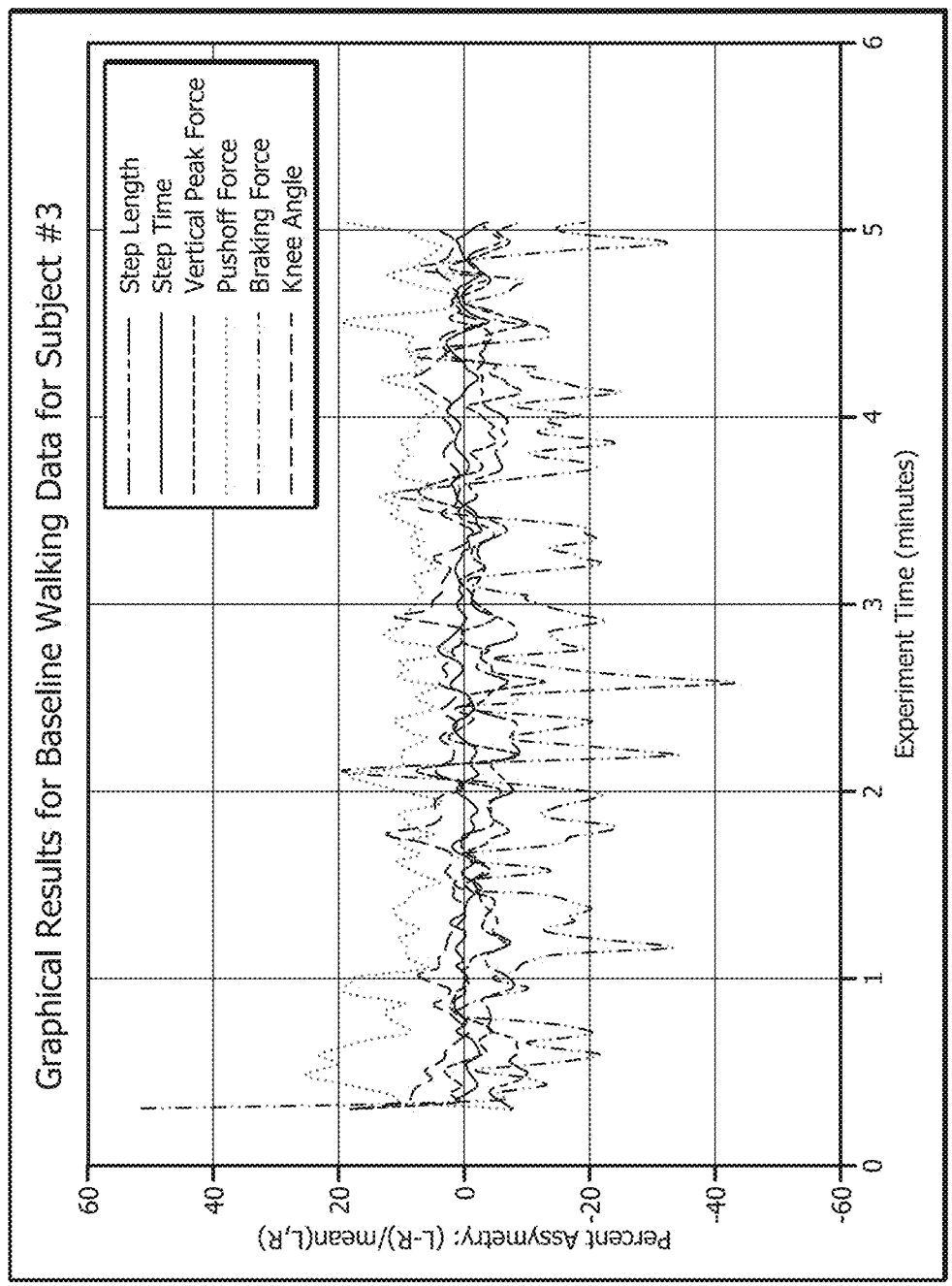
FIG. 3A is a depiction of normal baseline walking results for subject 3. This experimental test had a duration of 5 minutes.
Figure 3B:
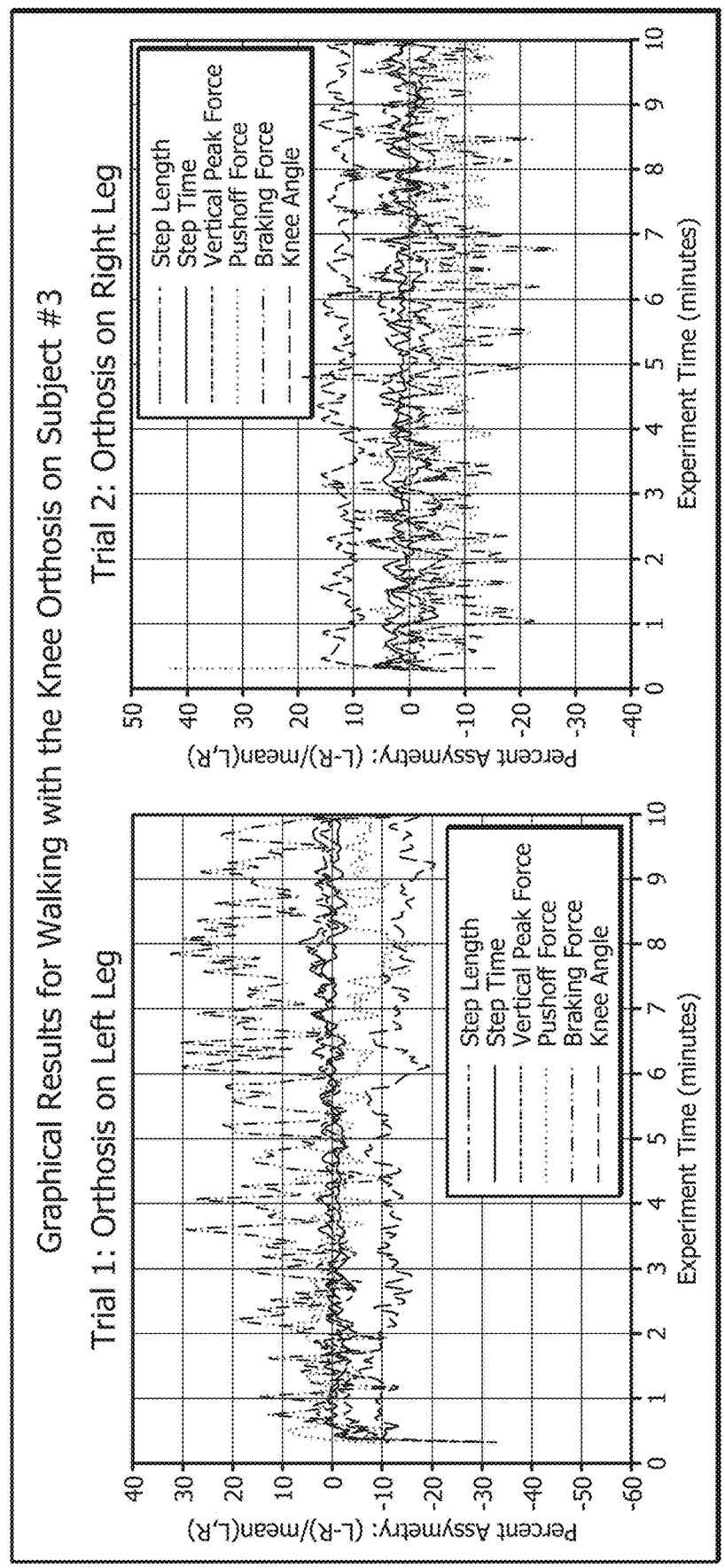
FIG. 3B is a depiction of walking with the knee orthosis results for subject 3. This experimental test had a duration of 10 minutes per leg. The left side of the figure presents the data from when the orthosis was positioned on the left leg. Similarly, the right side of the figure corresponds to the data obtained from when the orthosis was positioned on the right leg.
Figure 3C:
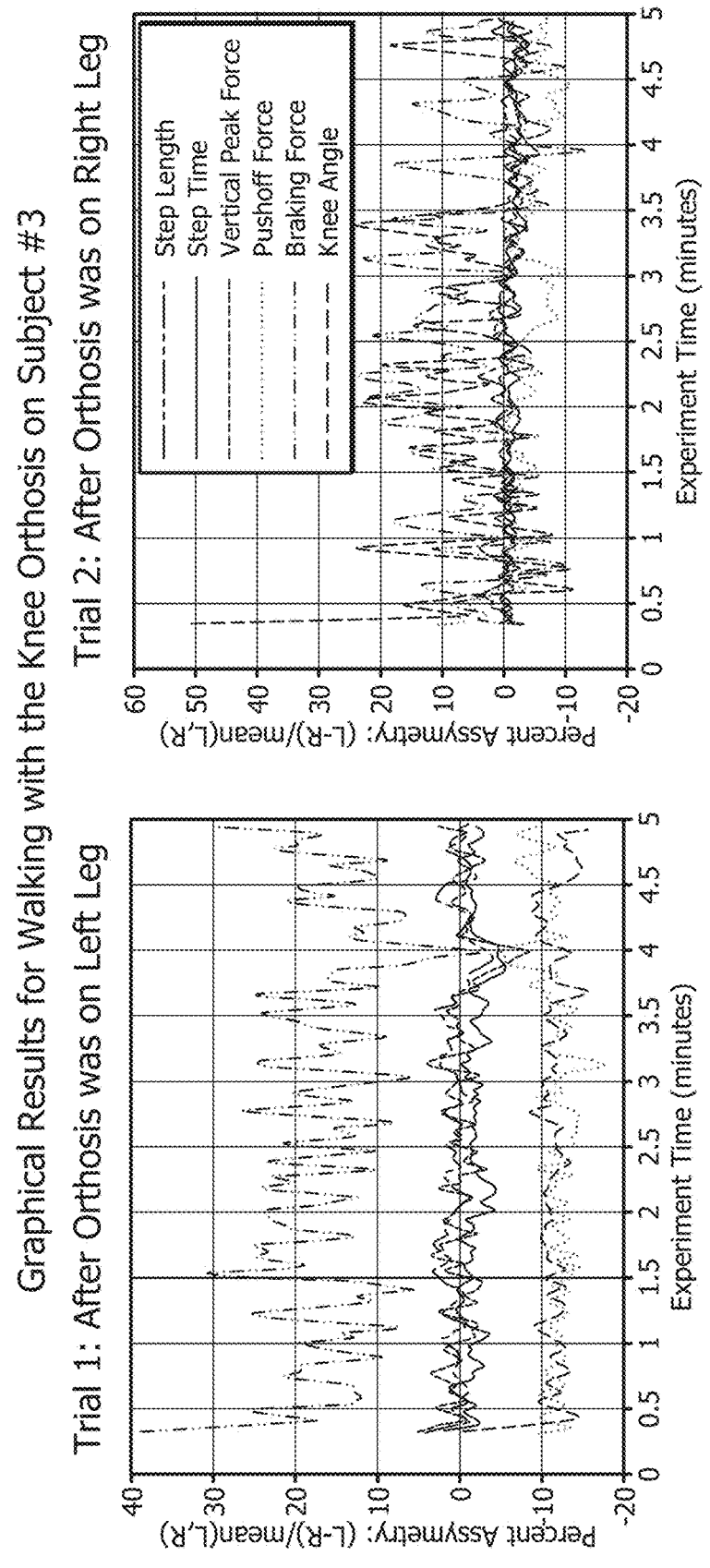
FIG. 3C is a depiction of the aftereffects of knee orthosis results for subject 3. This experimental test had a duration of 5 minutes per leg. The left side of the figure presents the data from immediately after the orthosis was removed from when it had been positioned on the left leg. Similarly, the right side of the figure corresponds to the data obtained immediately after the orthosis was removed from when it had been positioned on the right leg.

The data obtained from this experimental procedure varied from subject to subject due to the fact that each individual inherently has a slight inherent asymmetry that is different from one another. In FIG. 3A, which illustrates a particular subject's gait, these inherent asymmetries can be seen, along with pushoff and braking forces and knee angles associated with one subject's baseline walking. Comparing these findings to those seen in FIG. 3B, this subject was seen to have larger braking and pushoff forces and decreased knee angles while wearing the orthosis. However, there did not appear to be a significantly large increase in step time and step length. This may have been due the subjects adapting their gait to accommodate for the hindrances and acclimating to the velocity of the treadmill. An interesting discovery that can be seen in FIG. 3C was that depending on which side of the body the subject noted as being his dominant side, corresponding mainly to which type of handedness he associated himself as, that side seemed to recover slower after the orthosis had been removed from the subject. This was seen in two of the three subjects. It also appeared as though the device increased the knee flexion angle greatly immediately after it had been removed, and more so on the non-dominant side in certain cases.

Orthosis Design Based on Study.

An embodiment of the current invention used in the current study was a dual sided knee orthosis—one side including the stiffness and damping mechanism and the other side being unhindered. This embodiment can be seen correctly positioned on the knee of a subject in FIG. 1E. The side with the spring-damper mechanism included variable stiffness and damping. The other side was merely used as a guide and included a securing/fastening attachment located on the opposite side of the knee. A plurality (e.g., eight) of plastic belt buckles were utilized as fasteners to firmly secure the orthosis onto the thigh and calf of the subject, as well as around the upper and lower portions surrounding the patella. The straps being placed on the top and bottom portion of the orthosis permit a more accurate and secure positioning on the subject's leg. This also helped reduce the amount of displacement down the leg, due to the simple act of walking. The knee orthosis with variable stiffness and damping also has capability of being adjustable to each subject/user.

Referring specifically to the spring-damper mechanism, a magnetorheological fluid (MRF) may optionally be utilized in the damper when variable damping is desired (it was necessary to have variable damping for this study). When the MRF has a small current supplied to it, the fluid's viscosity increases, resulting in a viscoelastic solid. The appliance would utilize a small alkaline battery with a voltage around 12V, thus avoiding any large amount of associated weight from being added to the orthosis.

Additionally, the spring-damper mechanism may be replaced by a piston surrounded by the MRF, permitting a greater amount of damping when a small current is applied and increasing ability to generate or hinder hyper flexion of the knee.

Study 2

Figure 1E:
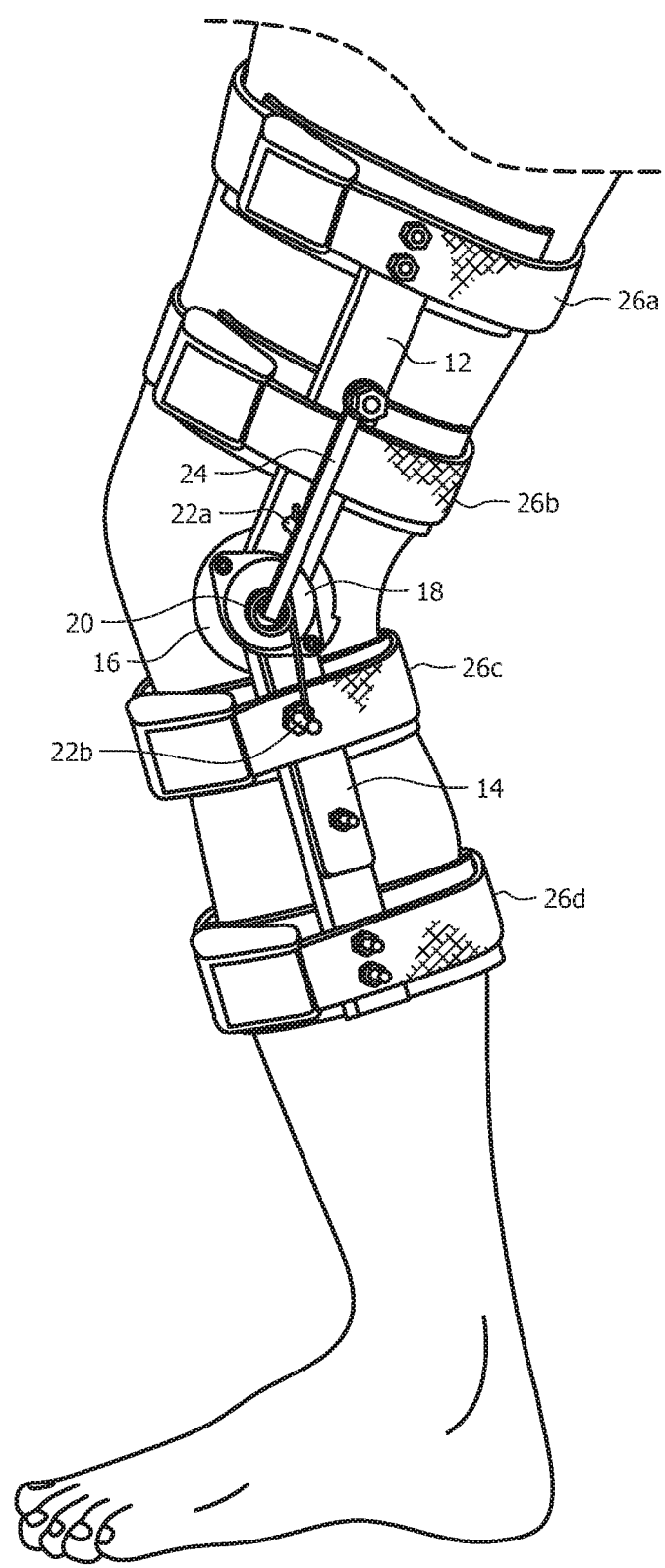
FIG. 1E depicts a knee orthosis positioned on knee of subject during testing procedure. The subject in this image was later markered and placed on the CAREN system.

Included in this study was a knee orthosis equipped with a spring-damper mechanism to convey variable stiffness and damping. The orthosis permitted evaluation of the effects of asymmetric dynamics of the knee on the gait patterns of healthy, able-bodied subjects. As noted, damping and stiffness of a person affected with stroke have been rated by the Modified Ashworth Scale, but it has not been quantified in terms of numerical values for stiffness and damping levels. The quantification of the Modified Ashworth Scale allows for a more personalized design of orthotics for aiding in rehabilitation. FIGS. 1A-1D again depict the knee orthosis used in this study, and FIG. 1E depicts it in use. In this preliminary experiment, the effects of one of the various combinations of damping and stiffness on the knee orthosis was studied.

It was an object of this study to create and implement a small, lightweight, and adjustable orthotic device to be positioned around the knee of an able-bodied person to simulate hemiparetic gait in order to quantify levels of the Modified Ashworth Scale. It was a further object of this study to develop a device that could easily and readily induce various levels of the Modified Ashworth Scale on an able-bodied subject via a spring-damper mechanism. The current orthosis, inducing hemiparetic gait, was tested using the CAREN system with five (5) able-bodied subjects with varying limb dominances. Force and motion capture data from the subjects were collected before, during, and after the subjects were fitted with the orthosis. The four parameters that the design on which the design was focused are damping, catch, hysteresis, and stiffness.

The device in this study was estimated to simulate about a 1+ on the Modified Ashworth Scale, which usually relates to a moderate-to-mild stroke. The preferred material used for the frame of the orthosis in this study was DELRIN, a plastic that has material properties similar to that of aluminum. The orthosis had a mounting that included slots and an adjustable connector that permitted for the rotary damper mechanism to easily be swapped with a different sized rotary damper, $\zeta=8898$ g-cm-s/°. In order to accommodate for variable stiffness, the orthosis was designed so that the connector piece was positioned in the center of the circular portion of a torsion spring, $K=0.457$ kg/mm, with a deflection angle of 90°. Both the upper and lower portions of the orthosis included two protruding bolts to lock the spring legs into place, thus facilitating replacement of the spring with other springs of various stiffnesses (e.g., for future testing of different stiffness levels). The damping and stiffness allow for the limited flexion at the knee joint to correspond with the limiting ranges of motion of the varying levels of the Modified Ashworth Scale.

Eight (8) plastic military belt buckles were used as fasteners to firmly secure the orthosis onto the thigh and calf of the subject, as well as around the upper and lower portions surrounding the subject's patella. The straps being placed on the top and bottom portions of the orthosis allowed for the orthosis to be positioned more securely and accurately on the subject's knee. It helped to reduce the amount of displacement down the leg during use.

Subjects.

Five (5) subjects volunteered to participate in this study of their own accord after having the experimental procedure and device described. The variable damping and stiffness were adjusted on the orthosis to simulate the specified level of the Modified Ashworth Scale. All subjects in this study declared themselves as possessing a dominant right leg. However, the testing was not exclusively limited to "right leg dominant" test subjects. One subject, the only female, was significantly shorter than the rest, which may have caused the orthosis to affect her gait more than other subjects since it encompassed a larger area of the subject's leg.

Experimental Procedure.

Generally, for each subject, data was gathered (1) for baseline, (2) with the orthotic device on the subject's non-dominant leg, and (3) with the orthotic device on the subject's dominant leg. Specifically, subjects walked at velocity that was calculated using a 10-meter walk test, thus establishing each subject's baseline walking velocity by taking an average of each subject's respective 10-meter walk tests. Using the CAREN system previously discussed, all subjects then walked with the orthosis for 10 minutes, and the aftereffects were recorded once the orthosis was removed.

Specifically, baseline symmetry was tested on the CAREN with the treads set at each subject's baseline velocity prior to being fitted with the orthosis. Each subject was fitted with a harness, positioned with infrared markers on predesignated areas of the body for motion capture, transferred to the platform via the ramp, and connected to the rail. The two treads were set to have the same speed, which was the subject's measured over-ground walking velocity. The treadmill began to move, and the subject was allowed a couple of minutes to become acclimated with the system in order make any adjustments prior to data collection. Data was then collected on any pre-existing spatial or temporal asymmetries, knee flexion angles, and ground reaction forces over a period of five (5) minutes.

After this "baseline walking" data had been collected, the orthosis was fitted onto the subject's non-dominant leg, and markers were placed on designated locations on the body. A depiction of the device positioned on the subject can be viewed in FIG. 1E. The evaluation continued by placing the subject on the CAREN system (see FIG. 2), harnessing and transferring him/her to the platform. The system was programmed to have the split belt treadmill velocities tied together and set at the subject's previously measured baseline velocity. Once the treadmill begins to move, the kinematic and kinetic data were collected and processed to find any spatial or temporal asymmetries, knee flexion angles, and ground reaction forces induced by the orthosis averaged over a period of ten (10) minutes.

Immediately following the trial with the orthosis on, the system was paused and the orthosis removed, while the subject was still on the treadmill. Post-orthosis data was obtained by having the subjects walk on the system for a period of 5 minutes. The expected aftereffect was that an increase in knee flexion of the affected knee would be observed, along with an increase in force profile that would dissipate within the first minute. Thus, it could be determined whether asymmetry was being induced through the use of the knee orthosis.

This process of obtaining data from the orthosis placed on the non-dominant leg was repeated but with the orthosis placed on the dominant leg. Both legs were tested for the purpose of analyzing if limb dominance was a factor to be considered in gait symmetry. The collected data from both legs was then analyzed to determine if the orthosis is a viable device to induce stroke-like gait patterns and asymmetries.

Results.

Figure 4:
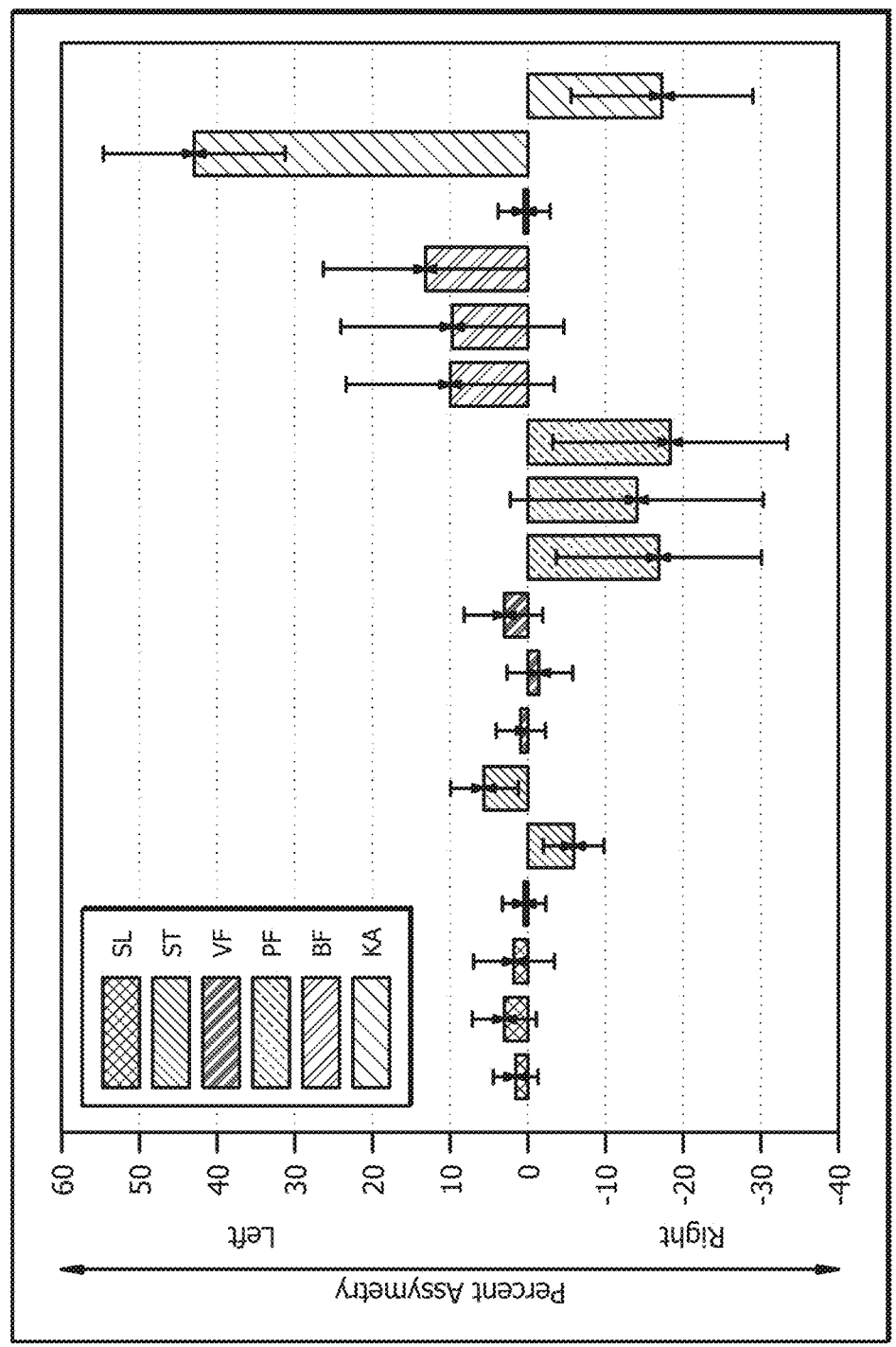
FIG. 4 is a bar graph comparing left/right asymmetries versus asymmetries in baseline gait parameters ($1^{st}$ bar in each set), gait parameters of the orthosis on the left knee ($2^{nd}$ bar in each set), and gait parameters of the orthosis on the right knee ($3^{rd}$ bar in each set).

The results of this study are summarized in FIG. 4. The measured parameters included step length (SL), step time (ST), average vertical force during stance phase (VF), pushoff force (PF), braking force (BF), and knee angle (KA). Each of these parameters were evaluated at baseline (i.e., when not wearing the orthosis), with the orthosis on the left leg, and with the orthosis on the right leg. The data can be viewed as follows: the first bar of each set represents the baseline asymmetry for that parameter, the second bar represents the asymmetry for the orthosis worn on the non-dominant left leg, and the third bar represents the asymmetry for the orthosis worn on the dominant right leg. The percent asymmetry left or right indicates an increased asymmetry toward that side of the body. Although the data obtained varied from subject to subject due to the fact that each person has an inherent asymmetry, the averages for all subjects were presented to demonstrate the trends associated with wearing the orthosis.

It can be seen in FIG. 4 and it was found herein that the orthosis altered an able-bodied person's gait, especially in the parameters of vertical forces, pushoff forces, braking forces, and knee angles. The results showed that the side with the orthosis had more time in stance phase, more vertical force, lower pushoff force, higher braking force, and significantly smaller knee angles. These are characteristics similar to stroke gait. It can also be seen in FIG. 4 that the direction of asymmetry for step length, push off, and braking forces were consistent. This may be an indication that the orthosis had no effect on these parameters with respect to the direction of asymmetry, which may be due to limb dominance amongst the subjects.

During the experiment, some subjects were observed extending the knee that was wearing the orthosis, especially when it was worn on the non-dominant knee, and there were some hysteresis effects that were observed in the aftereffect trials. However, there did not appear to be a significant change in step time and step length. This may have been due the subjects adapting their gait in order to accommodate for the hindrances and acclimate to the velocity of the treadmill. The leg on which the orthosis was worn made a difference in the resulting effect. After the orthosis had been removed, the non-dominant side returned to the baseline gait pattern more slowly. The orthosis also increased the knee flexion angle immediately after it had been removed from both legs (i.e., an aftereffect), but was significantly more pronounced on the non-dominant side.

The knee orthosis displayed the desired adjustability and precision for positioning on each user's body. Initial testing indicated a noticeable asymmetry while wearing the knee orthosis and immediately after wearing the knee orthosis, thus showing that it has the capability to alter an able-bodied person's gait, especially in the parameters of vertical forces, pushoff forces, braking forces, and knee angles. It also was able to induce some asymmetries for a short period of time (e.g., no more than a minute immediately after the orthosis was removed).

It can thus be understood that due to the knee orthosis inducing larger knee flexion as an aftereffect in able-bodied individuals, the orthosis can be utilized and applied as a rehabilitation device for individuals with stroke.

Glossary of Claim Terms

Damping effect: This term is used herein to refer to a reduction in the amplitude of oscillations felt by a user of the orthosis, where the oscillations resulted from energy being drained from the system to overcome resistive forces.

Increasing knee flexion: This term is used herein to refer to an elevated change in the angle between a user's thigh and the user's shin (or decrease in the angle between the user's thigh and the user's calf). In other words, an increase in knee flexion would allow the user to "bend his/her knee" more efficiently and effectively when walking.

Inner calf: This term is used herein to refer spatially to a medial aspect of the user's calf.

Inner thigh: This term is used herein to refer spatially to a medial aspect of the user's thigh.

Lateral side of the knee: This term is used herein to refer spatially to an outer aspect of the user's knee, not directly in front or behind the knee but to the outside.

Lower patellar region: This term is used herein to refer spatially to an area of the user's body in proximity to but just above the user's knee.

Medial side of the knee: This term is used herein to refer spatially to an inner aspect of the user's knee, not directly in front or behind the knee but to the inside.

Outer calf: This term is used herein to refer spatially to a lateral region of the user's calf.

Outer thigh: This term is used herein to refer spatially to a lateral region of the user's thigh.

Spring leg: This term is used herein to refer to one end of the spring member that extends outwardly from the coil of the spring member.

Spring post: This term is used herein to refer to any support structure for securing a spring leg thereto or therein.

Substantially parallel relation: This term is used herein to refer to the lengths of two objects or components being in the same general direction. For example, as can be seen in FIG. 1E, an upper splint of the orthosis is not depicted as directly parallel to the user's thigh, though it is "substantially" parallel. The same is true of the lower splint of the orthosis and the user's calf.

Upper patellar region: This term is used herein to refer spatially to an area of the user's body in proximity to but just above the user's knee.

Variable damping and stiffness: This term is used herein to refer to adjustable levels of stability (affecting number of oscillations felt by the user) and rigidity (affecting power needed for user to walk with knee flexion).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A knee orthosis with variable damping and stiffness for increasing knee flexion at a knee or knee joint of a user thereof, said knee orthosis comprising:
   a rigid or semi-rigid, elongate upper splint configured to be positioned in a substantially parallel relation to an outer thigh of said user;
   a rigid or semi-rigid, elongate lower splint configured to be positioned in a substantially parallel relation to an outer calf of said user;
   a central hub disposed between said upper splint and said lower splint and positioned on a lateral side of said knee of said user, where said upper splint and said lower splint are disposed in hinged relation to each other through said central hub;
   a rotary damper positioned on said lateral side of said knee of said user at a coupling point where said upper splint and said lower splint rotate relative to each other, said rotary damper providing a damping effect when said upper splint and said lower splint rotate relative to each other;
   a spring member positioned on said lateral side of said knee of said user at said coupling point where said upper splint and said lower splint rotate relative to each other, said spring member including an upper spring leg that is coupled to said upper splint and a lower spring leg that is coupled to said lower splint, said spring member providing a stiffness when said upper splint and said lower splint rotate relative to each other; and
   a monolithic connector spaced apart from said upper splint, said monolithic connector having a first portion and a second portion, such that said first portion and said second portion are a monolithic unitary structure forming said monolithic connector, said first portion disposed through a center of said spring member and positioned perpendicular to said second portion, said second portion disposed parallel to said upper splint and mounted onto said upper splint at a terminal end opposite the first portion, wherein said second portion is laterally spaced apart and parallel to said upper splint,
   wherein said monolithic connector is removable to access said spring member and said rotary damper for replacement.

2. A knee orthosis as in claim 1, further comprising:
   an upper spring post extending outwardly from said upper splint, wherein said upper spring leg is coupled to said upper splint by being secured to said upper spring post; and
   a lower spring post extending outwardly from said lower splint, wherein said lower spring leg is coupled to said lower splint by being secured to said lower spring post.

3. A knee orthosis as in claim 2, further comprising:
   said upper spring post and said lower spring post each being a bolt respectively disposed through said upper splint and said lower splint.

4. A knee orthosis as in claim 1, further comprising:
   one or more upper straps configured to secure said upper splint to said outer thigh of said user; and one or more lower straps configured to secure said lower splint to said outer calf of said user.

5. A knee orthosis as in claim 4, further comprising:
said one or more upper straps including a thigh strap configured to secure a superior end of said upper splint to a thigh of said user,
said one or more upper straps further including an upper patellar strap configured to secure an inferior end of said upper splint to an upper patellar region of said user,
said one or more lower straps including a lower patellar strap for securing a superior end of said lower splint to a lower patellar region of said user, and
said one or more lower straps further including a calf strap for securing an inferior end of said lower splint to a calf of said user.

6. A knee orthosis as in claim 1, further comprising:
a rigid or semi-rigid, elongate upper guide configured to be positioned in a substantially parallel relation to an inner thigh of said user;
a rigid or semi-rigid, elongate lower guide configured to be positioned in a substantially parallel relation to an inner calf of said user; and
a hinge disposed between said upper guide and said lower guide and positioned on a medial side of said knee of said user, where said upper splint and said lower splint are disposed in hinged relation to each other through said hinge,
wherein said upper guide and said lower guide are coupled to said upper splint and said lower splint, such that said upper guide and said upper splint move in unison and said lower guide and said lower splint move in unison.

7. A knee orthosis as in claim 1, further comprising:
said spring member being a torsion spring.

8. A knee orthosis as in claim 1, further comprising:
a magnetorheological fluid disposed within said rotary damper for increasing said damping effect.

9. A knee orthosis as in claim 1, further comprising:
said rotary damper disposed in outer relation to said central hub.

10. A knee orthosis as in claim 9, further comprising:
said spring member disposed in outer relation to said rotary damper.

11. A knee orthosis with variable damping and stiffness for increasing knee flexion at a knee or knee joint of a user thereof, said knee orthosis comprising:
a rigid or semi-rigid, elongate upper splint configured to be positioned in a substantially parallel relation to an outer thigh of said user;
a rigid or semi-rigid, elongate lower splint configured to be positioned in a substantially parallel relation to an outer calf of said user;
a central hub disposed between said upper splint and said lower splint and positioned on a lateral side of said knee of said user, where said upper splint and said lower splint are disposed in hinged relation to each other through said central hub;
a rotary damper; said rotary damper disposed in outer relation to said central hub and positioned on said lateral side of said knee of said user at a coupling point where said upper splint and said lower splint rotate relative to each other, said rotary damper providing a damping effect when said upper splint and said lower splint rotate relative to each other;
a magnetorheological fluid disposed within said rotary damper for increasing said damping effect;
a spring member disposed in outer relation to said rotary damper and positioned on said lateral side of said knee of said user at said coupling point where said upper splint and said lower splint rotate relative to each other, said spring member including an upper spring leg that is coupled to said upper splint and a lower spring leg that is coupled to said lower splint, said spring member providing a stiffness when said upper splint and said lower splint rotate relative to each other;
an upper spring post extending outwardly from said upper splint, wherein said upper spring leg is coupled to said upper splint by being secured to said upper spring post;
a lower spring post extending outwardly from said lower splint, wherein said lower spring leg is coupled to said lower splint by being secured to said lower spring post,
said upper spring post and said lower spring post each being a bolt respectively disposed through said upper splint and said lower splint;
a monolithic-connector spaced apart from said upper splint, said monolithic connector having a first portion and a second portion, such that said first portion and said second portion are a monolithic unitary structure forming said monolithic connector, said first portion disposed through a center of said spring member and positioned perpendicular to said second portion, said second portion disposed parallel to said upper splint and mounted onto said upper splint at a terminal end opposite the first portion, wherein said second portion is laterally spaced apart and parallel to said upper splint,
wherein said monolithic connector is removable to access said spring member and said rotary damper for replacement;
a thigh strap configured to secure a superior end of said upper splint to a thigh of said user;
an upper patellar strap configured to secure an inferior end of said upper splint to an upper patellar region of said user;
a lower patellar strap for securing a superior end of said lower splint to a lower patellar region of said user;
a calf strap for securing an inferior end of said lower splint to a calf of said user;
a rigid or semi-rigid, elongate upper guide configured to be positioned in a substantially parallel relation to an inner thigh of said user;
a rigid or semi-rigid, elongate lower guide configured to be positioned in a substantially parallel relation to an inner calf of said user; and
a hinge positioned between said upper guide and said lower guide and positioned on a medial side of said knee of said user, where said upper guide and said lower guide are disposed in hinged relation to each other through said hinge,
wherein said upper guide and said lower guide are coupled to said upper splint and said lower splint, such that said upper guide and said upper splint move in unison and said lower guide and said lower splint move in unison.

* * * * *